United States Patent [19]

Nohl et al.

[11] Patent Number: 4,957,009

[45] Date of Patent: Sep. 18, 1990

[54] PUSHLOOP LIQUID SAMPLING METHOD

[75] Inventors: Andre Nohl, Sunnyvale; Landy B. White, Sunol, both of Calif.

[73] Assignee: Spectra-Physics, Inc., San Jose, Calif.

[21] Appl. No.: 467,299

[22] Filed: Jan. 11, 1990

Related U.S. Application Data

[63] Continuation of Ser. No. 248,832, Sep. 23, 1988, abandoned.

[51] Int. Cl.$^5$ .............................................. G01N 1/14
[52] U.S. Cl. ............................ 73/864.84; 73/863.72; 436/180
[58] Field of Search ........... 73/863.71, 863.72, 863.73, 73/863.86, 864.81–864.87, 864.63, 864.64, 864.65, 864.66, 864.67; 422/103; 436/180

[56] References Cited

U.S. PATENT DOCUMENTS

| | | | |
|---|---|---|---|
| 2,981,092 | 4/1961 | Marks | 73/864.83 X |
| 3,122,168 | 2/1964 | Wright | 73/864.81 X |
| 3,530,721 | 9/1970 | Hrdina | 73/863.72 |
| 3,932,065 | 1/1976 | Ginsberg et al. | 417/388 X |
| 3,933,165 | 1/1976 | Budzak et al. | 73/864.83 X |
| 3,975,946 | 8/1976 | Ball et al. | 73/864.84 X |
| 3,991,055 | 11/1976 | Godin et al. | 73/864.84 X |
| 4,007,626 | 2/1977 | Roof et al. | 73/23.1 |
| 4,068,528 | 1/1978 | Gundelfinger | 73/864.84 |
| 4,620,452 | 11/1986 | Seki | 73/864.21 |
| 4,722,830 | 2/1988 | Urie et al. | 73/863.73 X |

FOREIGN PATENT DOCUMENTS

| | | | |
|---|---|---|---|
| 90260 | 7/1981 | Japan | 73/864.81 |
| 234336 | 10/1986 | Japan | 73/864.81 |
| 286751 | 12/1986 | Japan | 73/864.81 |
| 628421 | 10/1978 | U.S.S.R. | 73/863.73 |

Primary Examiner—Tom Noland
Attorney, Agent, or Firm—Skjerven, Morrill, MacPherson, Franklin & Friel

[57] ABSTRACT

A pushloop liquid sampling method is an improvement in the method of introducing liquid samples into test equipment (such as for liquid chromatography) via a six port valve. The method involves pulling the sample completely past the sample loop in the six port valve and then pushing the desired amount of sample back into the sample loop.

13 Claims, 3 Drawing Sheets

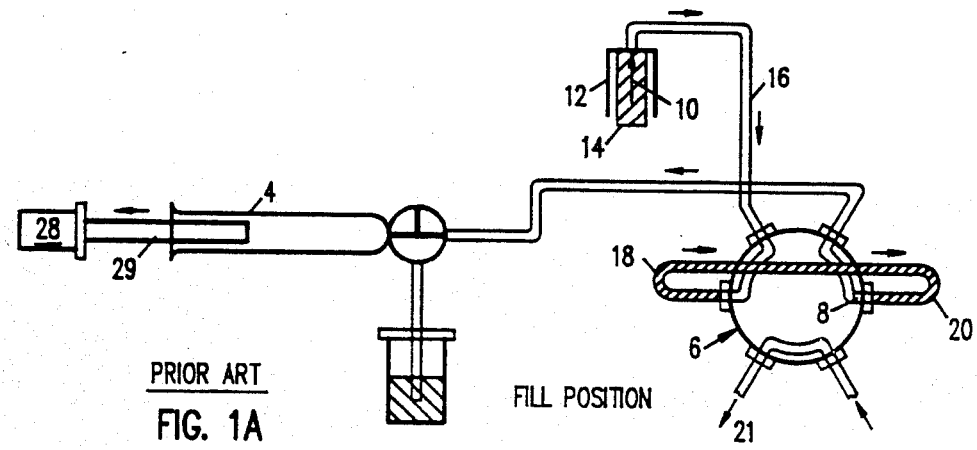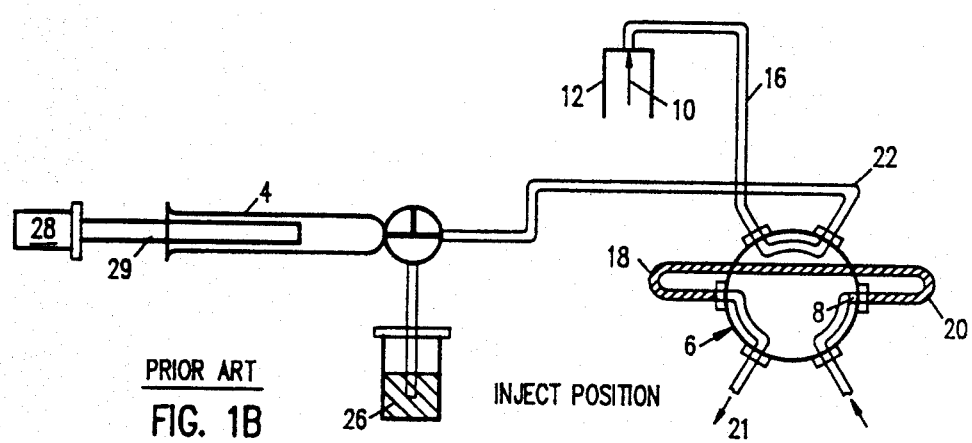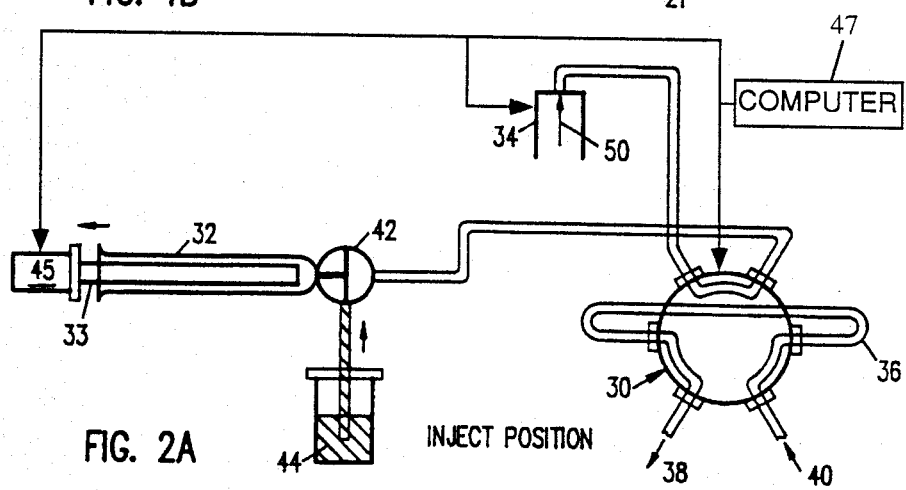

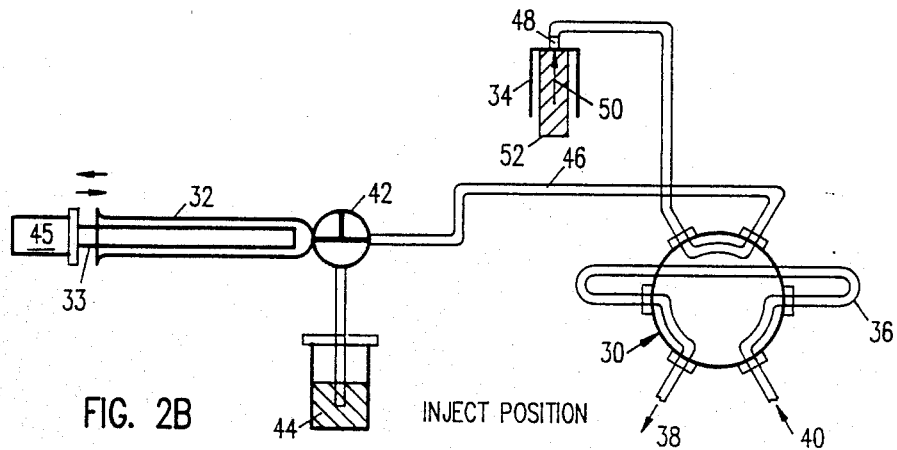
FIG. 2B INJECT POSITION
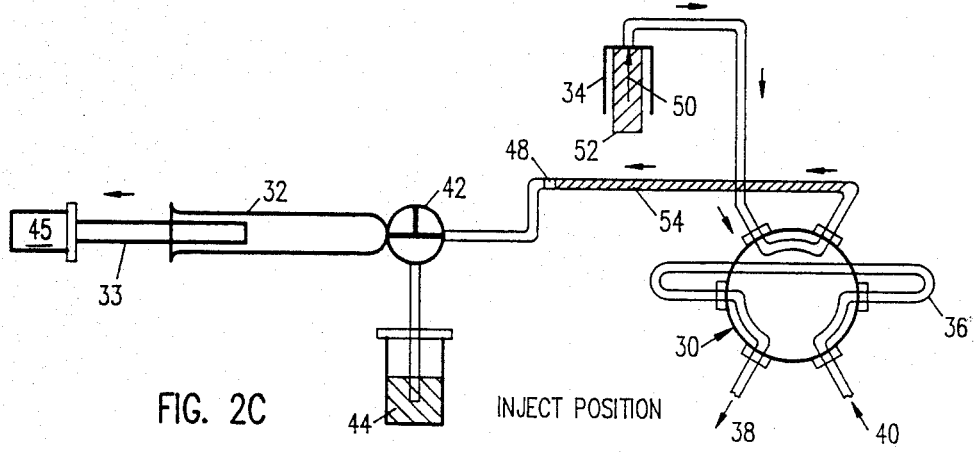
FIG. 2C INJECT POSITION
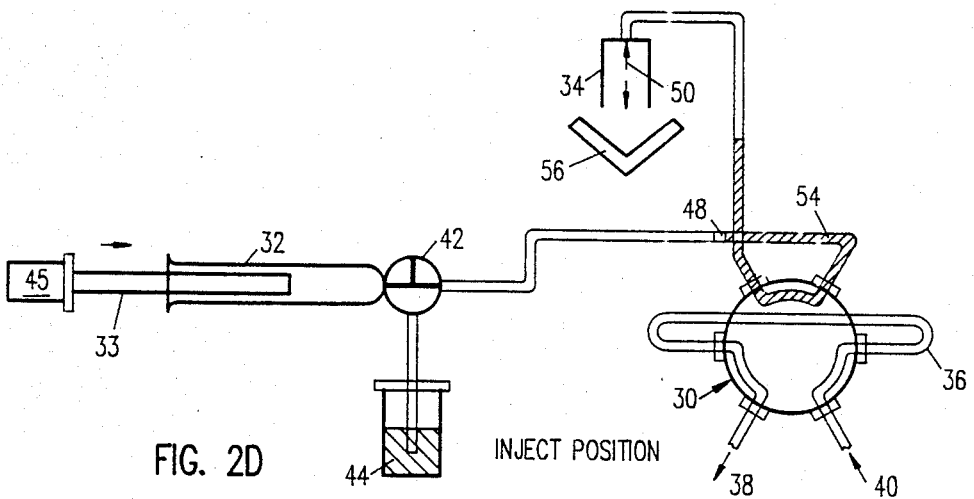
FIG. 2D INJECT POSITION

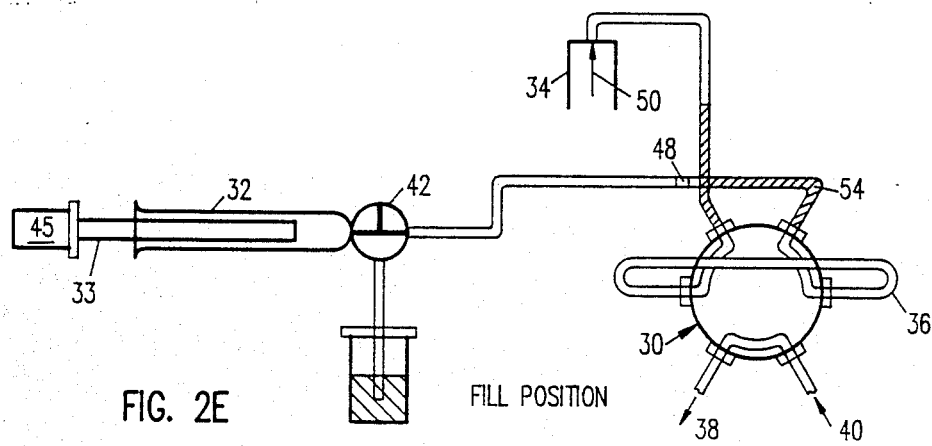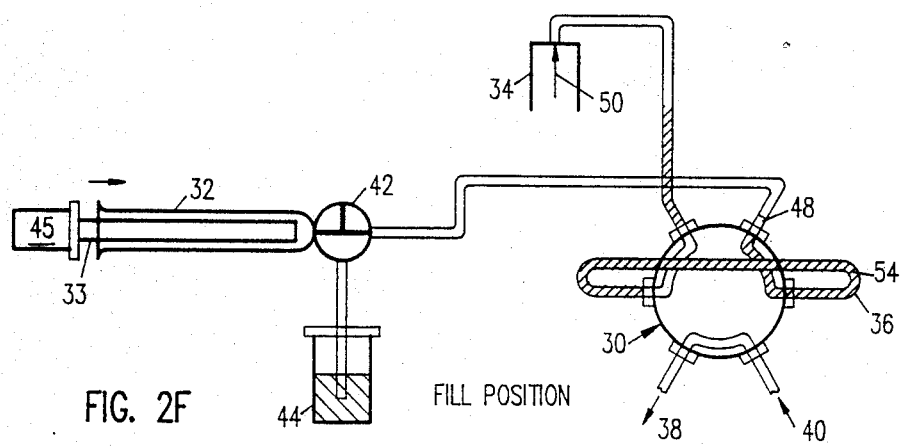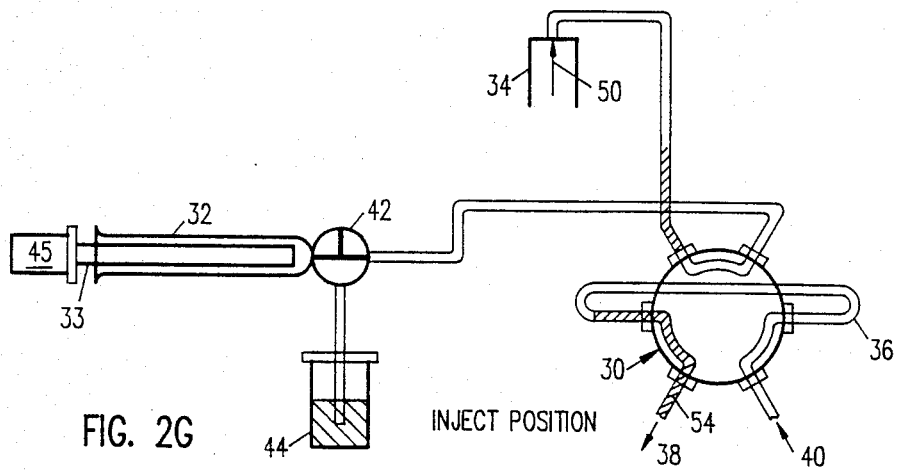

PUSHLOOP LIQUID SAMPLING METHOD

This application is a continuation of application Ser. No. 07/248,832, filed 09/23/88 and now abandoned.

BACKGROUND OF THE INVENTION

This invention is in the field of liquid sampling techniques, as used for example in liquid chromatography equipment or in blood testing equipment. The invention is an improvement in the method of introducing liquid samples into the equipment where a valve having at least six ports is used to perform sample loop injections.

The typical liquid sampling apparatus is as shown in FIG. 1.

The prior art method for doing sample loop injections with a typical liquid sampling apparatus is as follows as shown in FIG. 1A and FIG. 1B.

1. The plunger 29 of syringe 4 pushes forward a bit, with the six port valve 6, at "FILL".
2. The plunger 29 pulls a small air bubble 8 into the needle 10 in the sample tower 12.
3. The vial 14 is lifted into the sample tower 12.
4. The plunger 29 pulls the exact amount desired from the vial 14 (plus a small quantity such as 0.6 μL to account for loss on the walls of the tubing 16).
5. The vial 14 is lowered.
6. The plunger 29 then pulls the sample 18, with air bubble 8 ahead of sample 18, the precise distance into the sample loop 20.
7. The six port valve 5 is thrown to "INJECT" so the sample 18 can be analyzed in the remaining part of the equipment, including analytical column 21, as shown in FIG. 1B.

There are several possible problems associated with this routine. The first is the introduction of an air bubble into the sample loop 20 behind the sample slug 18. There is also the possibility of introducing unwanted air into the sample loop 20 ahead of the sample 18 if the sample 18 is pulled more than the exact amount. Air bubbles can be broken up and dispersed at connector junctions 22 causing inaccuracies in the sample draw.

The second is the possibility of leaving part of the sample 18 on the walls of the transport tubing 16 since this tubing 16 is not "swept" with solvent (hence the 0.6 μL offset) Also, to draw the correct amount of sample 18, the flush solvent 26 used to clean the system between samples must be completely degassed. Otherwise, there is the possibility of cavitation or outgassing when the plunger 29 is drawn back. This creates air bubbles which can make the volume of sample 18 drawn very inaccurate.

A major source of error concerns the design of the mechanical syringe drive 28. Even on a brand new system, where there is very little play in the screwdrive (not shown), the shuttle (not shown) that holds the plunger 29 can wobble when the lead screw (not shown) rotates. Over a period of time, the drive 28 will wear and more "slop" is introduced. This affects the accuracy of the volume of sample 18 drawn as well as the reproducibility of the sample volume over time.

SUMMARY OF THE INVENTION

In an attempt to improve long-term reproducibility and accuracy, a novel method for sample loop injections was devised and tested.

The novel method involves pulling the sample completely past the sample loop and then pushing the correct amount back in. The routine is as follows:

1. Pull a small amount of flush solvent into the syringe from the reservoir of flush solvent, thus taking care of backlash in the syringe drive.
2. Switch the syringe to the transport tubing leading to the sample tower. Then pull a small air bubble into the needle which is in the sample tower. The vial is lifted into the sample tower.
3. With the six port valve in the "INJECT" position, pull enough sample past the six port valve so that the desired amount of the sample can be pushed back.
4. Then a small amount of the sample is pushed back to take up backlash in the syringe drive mechanism.
5. The six port valve is switched to the "FILL" position.
6. The desired volume of the sample is pushed back into the sample loop.
7. The six port valve is switched back to the "INJECT" position, and the desired volume of the sample is injected into the analytical column.

The method of the present invention thus uses the same apparatus as the prior art, but includes a novel series of steps.

The benefits of the present invention over the prior art include:

1. Better linearity.
2. Better precision.
3. Better accuracy of volume.
4. No need for degassing the flush solvent.
5. A cleaner test baseline, due to elimination of air bubbles. Air bubbles, when injected, create artifacts on the baseline early in the analytical process.

BRIEF DESCRIPTION OF THE DRAWINGS

FIGS. 1A and 1B show a typical liquid sampling apparatus, and the prior art method of sampling.

FIGS. 2A, 2B, 2C, 2D, 2E, 2F and 2G show the steps of the method of the present invention.

DETAILED DESCRIPTION OF THE INVENTION

FIG. 2A shows the same arrangement of liquid sampling apparatus as shown in FIG. 1. The six port valve 30 has two positions: "FILL" wherein the syringe 32 is connected to the sample tower 34 via sample loop 36, and "INJECT" wherein the sample loop 36 is connected to the test column 38 with a fluid return for the sample by means of pump 40. Three way valve 42 connects the reservoir 44 of the flush solvent to syringe 32. This computer 47 controls the entire system by well known methods (Computer 47 and the associated control lines as shown in FIG. 2A are understood to be present in FIGS. 2B to 2G but are not shown for simplicity). Valve 30, syringe 32, and valve 42 are controlled conventionally by computer 47.

The method of the present invention includes the following steps:

First, as shown in FIG. 2A, three way valve 42 is switched so as to connect the reservoir 44 of flush solvent to syringe 32. Plunger 33 of syringe 32 is withdrawn so as to pull a small amount of flush solvent, typically 3 μL, into syringe 32. The amount of flush solvent pulled by the plunger 33 must be enough to account for backlash in the drive mechanism 45 for syringe 32.

Second, in FIG. 2B, three way valve 42 is switched so syringe 32 is connected to transport tubing 46. Six port valve 30 is in the "INJECT" position. The three-way valve 42 is closed so the flush reservoir 44 is no longer connected to syringe 32. The plunger 33 is withdrawn so as to pull a small air bubble 48 into needle 50. Then sample vial 52 is lifted into the sample tower 34.

Third, in FIG. 2C, the desired amount of sample 54 (such as 30 μL for a 10 μL injection) is drawn out of sample vial 52 by further withdrawing plunger 33. Sample 54 is preceded by air bubble 48. Then sample vial 52 is lowered out of sample tower 34.

Fourth, in FIG. 2D, a flush funnel 56 is moved into the sample tower 34. Then plunger 33 is pushed back so as to take up mechanical backlash in the syringe drive mechanism 45; typically this push back will push about 3 μL of the sample 54 into the flush funnel 56, to be disposed of.

Fifth, in FIG. 2E, six port valve 30 is switched to the "FILL" position.

Sixth, in FIG. 2F, the plunger 33 is pushed back to push the desired volume 54 of sample into the sample loop 36. Bubble 48 is not pushed into the sample loop 36.

(That part of the sample 54 not pushed into the loop 36 is flushed to waste after the sample 54 is injected as described below.)

Seventh, in FIG. 2G, six port valve 30 is switched to the "INJECT" position. Sample volume 54 then moves into analytical column 38. After analysis, the analyzed sample 54 is flushed to waste, as is that part of the sample 54 which was not pushed into sample loop 36.

In the preferred embodiment, the above method is automated by a computer that controls the entire system of liquid test equipment by well-known methods. In this case, implementation of the invention is a matter of modifying the computer's software.

Other embodiments of the invention will be apparent to one of ordinary skill in the art. For instance, the syringe could be replaced by any metering device. Also, the six port valve could have additional ports.

The above description of the invention is illustrated and not limiting. Further modifications and equivalents may be employed without departing from the true spirit and scope of the invention.

We claim:

1. A method of transferring a liquid sample from a reservoir to an analytical column by means of a valve having a body and having at least two position comprising the steps of:
   drawing the sample from the reservoir through a needle;
   passing the sample from the needle through the valve in a first direction with the valve in a first position;
   switching the valve to a second position;
   passing only a portion of the sample into the valve in a second direction; and
   then injecting the portion of sample into the column; wherein at all times the needle is stationary relative to the body of the valve.

2. The method of claim 1, wherein a metering device is used in passing the sample into the valve at least in the second direction.

3. The method of claim 2, wherein the metering device is a syringe.

4. The method of claim 2, further comprising the step of partially filling the metering device with a solvent so as to account for backlash in the metering device prior to the first mentioned step.

5. The method of claim 2, further comprising the step of taking up backlash in the metering device prior to the step of switching the valve.

6. The method of claim 2, wherein the valve includes a sample loop, and the first valve position disconnects the metering device from the sample loop, and the second valve position connects the metering device to the sample loop.

7. The method of claim 2, further comprising the step of preventing any of the sample from entering the metering device.

8. A method of claim 1, wherein the valve includes at least six ports and a needle does not extend into any of the ports.

9. The method of claim 8, wherein the valve includes a sample loop.

10. The method of claim 1, wherein the steps are under control of computer means.

11. The method of claim 1, further comprising the step of switching the valve to the first position after the step of passing the sample into the valve.

12. The method of claim 1, further comprising the step of passing the sample out of the valve after the step of passing the sample into the valve in the second direction.

13. The method of claim 1, further including the steps of:
   providing a metering device having a stroke for metering a particular volume for passing the sample through the valve; and
   wherein the portion of the sample injected into the column is an amount less than that metered by one stroke of the metering device.

* * * * *